United States Patent [19]

Shamsuddin et al.

[11] Patent Number: 4,857,457

[45] Date of Patent: Aug. 15, 1989

[54] SCREENING TEST FOR LARGE INTESTINAL CANCER

[76] Inventors: Abulkalam M. Shamsuddin, 2916 Old Court Rd., Baltimore, Md. 21208; Alaaeldeen M. Elsayed, 6458 Root Dr., Glen Burnie, Md. 21061; Glenn A. Jockle, 511 S. Sharp St., Baltimore, Md. 21201

[21] Appl. No.: 889,022

[22] Filed: Jul. 24, 1986

[51] Int. Cl.$^4$ .......................... C12Q 1/26; C12Q 1/54; G01N 33/543; G01N 33/574
[52] U.S. Cl. ......................................... 435/7; 435/14; 435/25; 435/810; 436/501; 436/518; 436/808; 436/813; 436/827
[58] Field of Search ...................... 435/7, 25, 810, 14; 436/501, 518, 64, 94, 533, 534, 808, 813, 827

[56] References Cited

U.S. PATENT DOCUMENTS 4,334,017 6/1982 Plotkin et al. .................... 436/827
4,571,382 2/1986 Adachi ............................... 436/827

OTHER PUBLICATIONS

Boland et al., Proc. Nat'l. Acad. Sci. U.S.A., 79, "Alterations In Human Colonic Mucin Occurring With Cellular Differentiation and Malignant Transformation", 2051–2055 (1982).

Hjelm et al., *Methods of Enzymatic Analysis*, vol. 3, Academic Press, Inc., New York, 1282–1287 (1974).
Lehman et al., Cancer, 53(2): 272–277, "Peanut Lectin Binding Sites In Transitional Cell Carcinoma of the Urinary Bladder" (1984).
L. C. Hoskins & E. T. Boulding, J. Clin. Invest 67: 163–172 (Jan. 1981).

*Primary Examiner*—Esther M. Kepplinger
*Attorney, Agent, or Firm*—Haight & Associates

[57] ABSTRACT

The disaccharide β-D-Gal (1->>3)-D-GalNAc, which specifically binds with peanut agglutinin (PNA) or oxidized by galactose oxidase, has been discovered in the colorectal mucus of patients with cancer or precancer. Because of the presence of β-D-Gal-(1>>3)-D-GalNAc also on neuraminidase treated erythrocytes of the ABO type, their competitive binding with PNA has been exploited to develop a hemagglutination inhibition assay. Additional methods of simple detection of this disaccharide include a latex agglutination test, enzyme-avidin-biotinylated PNA, and a galactose oxidase strip test. This rapid, simple and inexpensive assay is designed to test the presence of β-D-Gal-(1>>3)-D-GalNAc in large intestine mucus obtained by routine digital-rectal examination and has the potential for screening populations for large intestinal carcinomas.

16 Claims, 2 Drawing Sheets

NORMAL

Normal mucus without
β-D-Gal (1→3)-D-Gal NAc

'T' antigen exposed
erythrocytes are agglutinated

Mucus with
β-D-Gal (1→3)-D-Gal NAc
binds peanut agglutinin

'T' antigen exposed erythro-
cytes are not agglutinated

SCREENING TEST FOR LARGE INTESTINAL CANCER

DESCRIPTION OF THE INVENTION

1. Technical Field of the Invention

This invention relates to a screening test for large intestinal cancer by detecting the presence of the disaccharide $\beta$-D-Gal-(1->>3)-D-GalNAc in large intestinal mucus.

2. Background Art

Cancer of the colon, cecum, and rectum (large intestinal cancer) is a major cause of morbidity and mortality in Western society. Large intestinal cancer is the second most common form of cancer in males and the third most common in females in the United States, with 138,000 new cases and 60,000 related deaths in 1985. Colon or rectal cancer eventually develops in approximately 6% of the U.S. population, and it has been estimated that some six million Americans who are alive in 1986 will die of it. Because there is currently no effective method for treating large intestinal cancer, the American Cancer Society's (ACS) guidelines recommend large intestinal cancer screening, an opinion which is also supported by others at the National Cancer Institute (NCI).

Based on the observation that large tumors are associated with bleeding, the fecal occult blood test is the current empirical screening test for cancer of the large intestine. The indirect nature of this test, which detects bleeding rather than cancer or other physiological changes which are more closely related to cancer, gives it an inherent inaccuracy because not all tumors bleed, nor are all bleedings due to cancer. Cancers that are large enough to bleed are more than likely to be advanced, so that the fecal occult blood test is not well suited for early cancer detection. Furthermore, not every malignant change in the large intestinal will be bleeding at the time the test is applied, nor will such bleeding necessarily be detected in the stool, especially if the site of bleeding is in the proximal segments of the colon.

The fecal occult blood test gives very high false negatives and false positive results. Indeed, a recently completed mass screening test involving 45,668 people reported by Winchester et al. (1983, CA 33:333–343) demonstrated that a mere 4.3% were positive. A false positive fecal occult blood test can easily occur, inter alia, because of ingestion of certain foods and drugs.

The disaccharide $\beta$-D-Gal-(1->>3)-D-GalNAc, also known as T-antigen, has been recently demonstrated to be expressed in the malignant and premalignant colonic epithelia in humans and in experimental animals but absent in the normal epithelia. Peanut (*Arachis hypogaea*) agglutinin (PNA) has specificity for T-antigen. Following neuraminidase treatment, erythrocytes of the human ABO type are agglutinated by PNA due to binding with cell surface T-antigen. At stoichiometric concentrations, PNA barely causes the red blood cells to agglutinate and fails to do so if a solution containing the T-antigen is added to the system, leading to agglutination inhibition.

Assays for enzymatic activity in colonic biopsy material are invasive, have a high cost, and entail the use of complicated procedures in a well equipped central laboratory, which make these assays unsuited as screening tests.

While T-antigen has been reported to be associated with a number of different types of cancer tissue, it has not heretofore been reported to be present in extracellular body fluids which have accordingly not been employed as a sample to test for the presence of T-antigen associated with cancer.

DISCLOSURE OF THE INVENTION

Accordingly, it is a general object of the present invention to provide a diagnostic test for large intestinal cancer that does not suffer from the above-indicated deficiencies of the prior art.

Another object of the present invention is to provide a diagnostic test for large intestinal cancer which does not give a high percentage of false positive and false negative readings.

A further object of the present invention is to provide a diagnostic test for large intestinal cancer which detects a biochemical change directly associated with large intestinal cancer.

An additional object of the present invention is to provide such a test which can detect large intestinal cancer in its early stages prior to development of a bleeding tumor.

A more particular object of the present invention is to provide a kit by means of which such a test can be conducted outside of a hospital or medical laboratory setting.

Upon study of the specification and appended claims, further objects, features and advantages of the present invention will become more fully apparent to those skilled in the art to which this invention pertains.

BEST MODE FOR CARRYING OUT THE INVENTION

Briefly, the above and other objects, features and advantages of the present invention are attained in one aspect thereof by providing a method for detecting the presence of precancer or cancer in the large intestine, which comprises obtaining a sample of rectal mucus; assaying said sample to quantitatively detect the presence of the disaccharide $\beta$-D-Gal-(1->>3)-D-GalNAc therein; and diagnosing the presence and degree of precancer or cancer based upon the amount of said disaccharide detected in the mucus. In a simple embodiment, the assay may be performed by use of a hemagglutination inhibition test, preferably by reacting the mucus with a precise amount of peanut agglutinin or other specific binding moiety for the disaccharide and then detecting the presence of unbound moiety. The reactant moiety can be immobilized onto a water-insoluble support, such as a membrane filter (e.g., immobilizing rectal mucus on a protein-capturing membrane filter) or solid beads of latex, plastic, glass, etc. In order to increase the sensitivity of the method, the reactant moiety can first be biotinylated in a conventional manner. The complex can be detected by any of various suitable techniques, either directly or indirectly, e.g. immunologically, enzymatically, oxidation-reductively, etc. Presently preferred is the formation of a complex with avidin conjugated to a suitable marker, e.g. fuchsin or other dyes, radioactive labelling, fluorescent dyes such as fluorescein isothiocyanate or Rhodamine B, luminescent dyes such as luciferol, luminol, biotin, etc.

The presence of the disaccharide is readily detected by agglomeration of sensitized beads which have been coated with PNA, e.g. glass, agarose, polystyrene, latex, etc. A preferred method for detecting the presence of the complex is by selectively oxidizing the sugar moiety of the disaccharide, e.g. with galactose oxidase, and detecting the presence of the oxidized sugar therein.

Absorption of the mucus sample onto a protein—capturing membrane filtering material has numerous advantages. For one thing, these samples appear to be quite stable and can be assayed days or weeks after being stored at or below room temperature without any significant deviation in results. In a preferred embodiment of the invention, a kit is provided which comprises separate containers of galactose oxidase, a protein-capturing membrane filter, basic fuchsin, and optionally deionized distilled water. Preferably the galactose oxidase is in lyophilized form, especially when impregnated onto a porous support such as filter paper, which can then be wetted and contacted directly with the rectal mucus sample on the membrane filter, then visualized by staining with fuchsin.

BRIEF DESCRIPTION OF THE DRAWINGS

Referring to the annexed drawings, like or corresponding reference characters refer to like or corresponding parts in the several figures, wherein.

DETAILED DESCRIPTION

This large intestinal cancer assay test detects a specific biochemical change in large intestinal mucus associated with cancer of the large intestine. The present inventors have discovered that the disaccharide $\beta$-D-Gal-(1->>b 3)-D-GalNAc, also known as T-antigen, is absent in the large intestinal mucus of normal individuals but present in patients with large intestinal cancer and precancer. The inventors then developed various techniques for the detection of this sugar moiety in a rapid, simple and inexpensive manner. These newly developed techniques were then tested to screen individuals for large intestinal diseases including cancer.

The lectin, peanut agglutinin (PNA) specifically binds with T-antigen and causes agglutination of T-antigen activated RBC. Exploiting these characteristics of PNA, initially a simple inhibition assay has been developed wherein T-antigen in large intestinal mucus will bind with PNA and, therefore, PNA will not react with RBC and the red cells will accordingly not agglutinate.

This test is very simple and can be performed rapidly. Using microtiter plates, a large number of samples can be screened in a short time. The galactose oxidase test can be done conveniently on a strip of membrane filter. Unlike the empirical fecal occult blood test which has very high false positive and false negative values, this test is based on specific biochemical abnormality of large intestinal mucus which the inventors have found to be associated with cancer and precancer.

Figure 1:
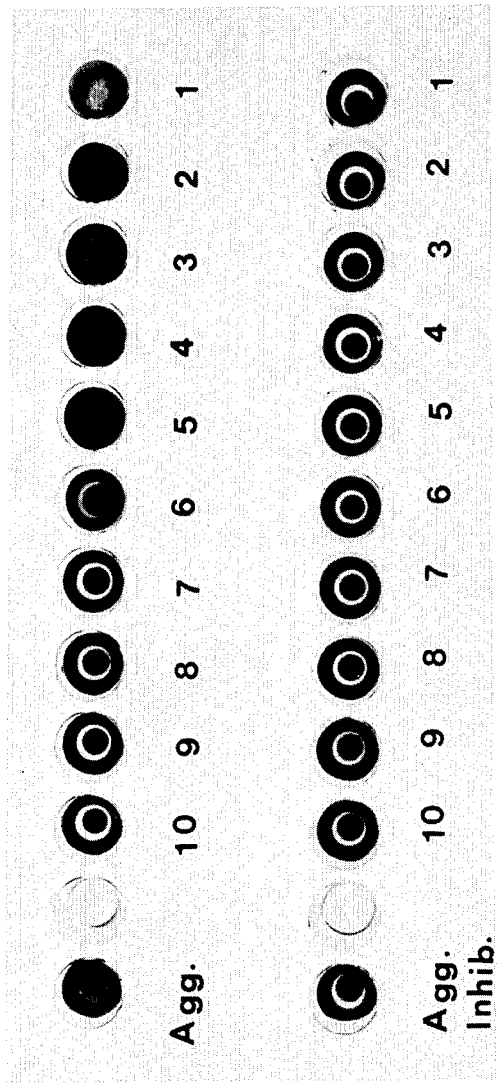
FIG. 1 is a photograph of a microtitration plate in which hemagglutination test is performed by mixing PNA, mucus, and T-antigen activated erythrocytes.

Mucus was obtained from patients with large intestinal cancer and healthy subjects free of large intestinal cancer during routine digital rectal examination. The mucus on the gloved finger was mixed with phosphate buffered saline (PBS). A hemagglutination test was performed by mixing PNA, mucus and T-antigen activated erythrocytes (FIG. 1). The assay conditions were optimized by using serial dilutions of PNA and a fixed volume of T-antigen activated erythrocytes, since PNA has only a limited binding capacity for T-antigen. It was determined that a PNA concentration of 2.5 micro g /ml barely causes hemagglutination of 50 micro l T-antigen activated erythrocytes recognizable after 1 hour of incubation which is inhibited by the trace amount of disaccharide present in the mucus of cancer and precancer patients.

Figure 2:
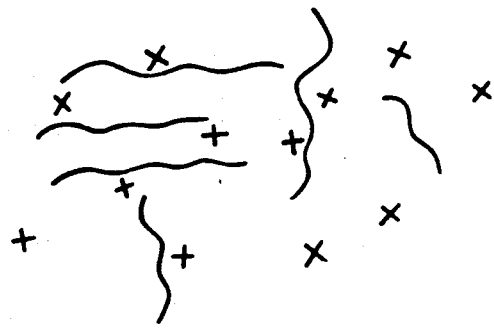
FIG. 2 is a schematic representation of the principle of the large intestinal cancer assay of this invention.
Figure 2:
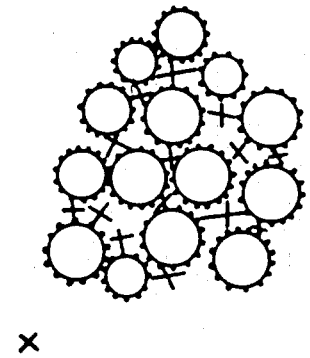
Figure 2:
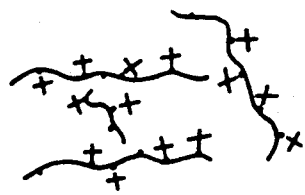
Figure 2:
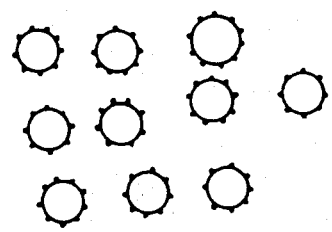
Figure 3:
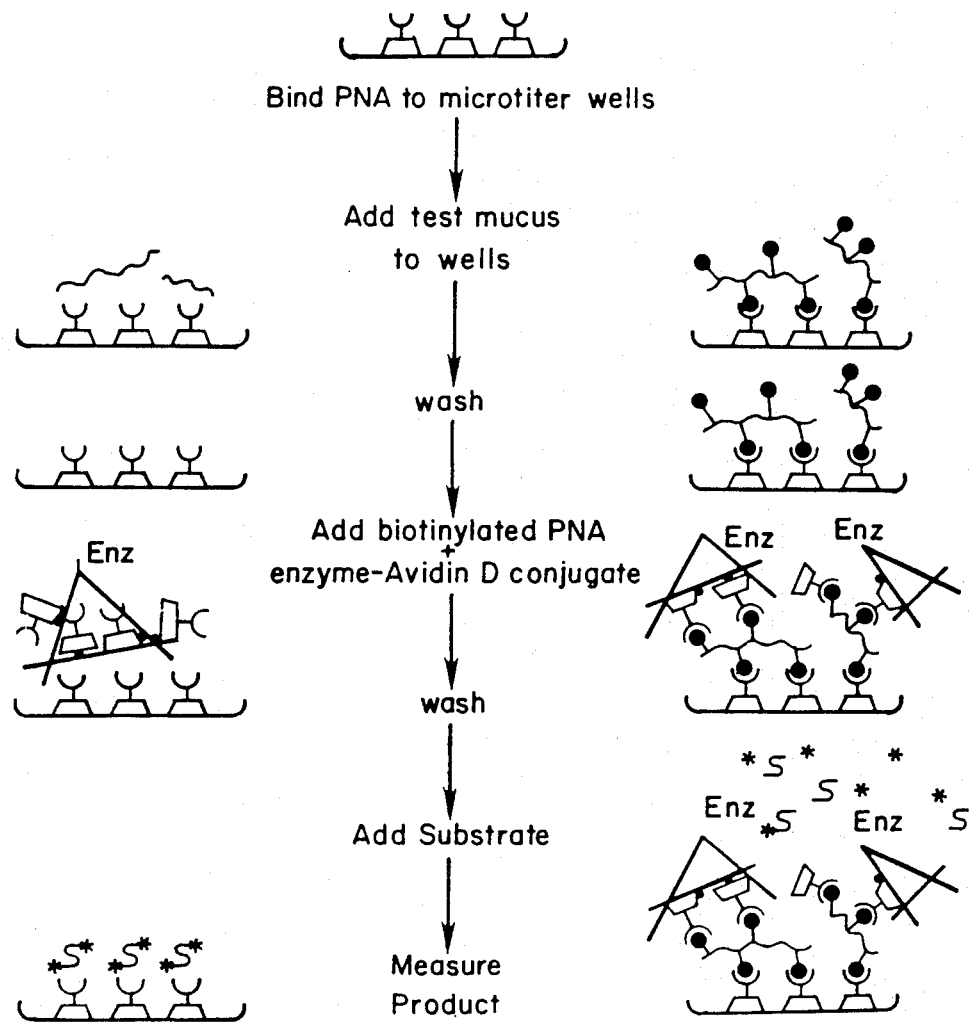
FIG. 3 is a schematic representation of the biotinylated PNA-Avidin enzyme assay of this invention.

FIG. 2 is a schematic representation of the principle of this assay. Upper panel: normal mucus glycoprotein (strands) not having recognizable $\beta$-D-Gal-(1->>3)-D-GalNAc fails to bind with PNA which in turn binds with T-antigen on activated erythrocytes causing agglutination. Lower panel shows cancer-associated mucus glycoprotein containing $\beta$-D-Gal(1->>3)-D-GalNAc which readily binds with PNA. At optimal PNA concentration, all binding sites will be blocked by the available disaccharide and therefore none will be available for binding with T-antigen on the erythrocytes, hence agglutination will be inhibited.

A pilot study using mucus obtained during digital rectal examination from 25 individuals showed an inhibition of agglutination in six patients with cancer and polyps and five with no obvious polyps or cancer. The remaining 14 patients (ages 54–89) were known to be free of any large intestinal cancer and showed no inhibition of agglutination (Table I). One patient (age 89) with diverticulosis was negative, indicating that diverticulosis and/or old age per se do not necessarily cause an agglutinatin inhibition reaction.

In addition to cancer, this test has the power to detect other diseases of the colon including those that carry a high risk of cancer such as fistula, ureterosigmoidostomy, Crohn's disease, and ulcerative colitis. Virtually no false negativity and a low (26%) false positive reaction renders this assay more suitable than the fecal occult blood test for population screening.

Other properties, such as immobilization of PNA onto a water-insoluble support, and oxidation of the sugar moiety and detection of the oxidized product by dyes, radio-chemicals, etc. can be exploited to develop additional assays.

Avidin, a glycoprotein (67,000 MW) has an extraordinarily high affinity for the vitamin biotin. Inasmuch as biotin molecules can be coupled to various proteins (biotinylation), avidin can be conjugated with various markers such as enzymes, dyes, heavy metals, radioactive isotopes, etc. Avidin has four binding sites for biotin, and many biotin molecules can be incorporated on a given protein. The present inventors have exploited this amplification principle to detect minute amounts (i.e. ng/ml or even pg/ml) of the marker disaccharide $\beta$-D-Gal-(1->>3)-D-GalNAc in mucus glycoproteins obtained during digital rectal examination. An assay was developed according to the following rationale: Mucus glycoprotein containing the specific disaccharide will avidly bind to the PNA immobilized on a solid phase. A matrix formed by biotinylated PNA and enzyme-avidin D conjugate will bind to residual disaccharides on the immobilized glycoprotein PNA, while a suitable substrate will amplify the reaction.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

EXAMPLE 1

Hemagglutination Inhibition Test

This technique uses PNA-T activated RBCs agglutination inhibition assay to test for the presence of this sialic acid free terminal sugar residue, utilizing the specific affinity of PNA to bind to the terminal galactose residue and more preferentially (by an affinity several orders of magnitude greater) to the terminal dimer $\beta$-D-Gal-(1->>3)-D-GalNAc as the binding of this lectin requires a free hydroxyl group at C-2. Mucus was obtained during digital rectal examination by inserting the saline lubricated gloved index finger of the physician. The finger containing the mucus was then dipped in a specimen bottle containing 500 micro l phosphate buffered saline PBS pH 7.2. The finger was rinsed thoroughly in the PBS to allow maximum extraction of the mucus from the glove. Hemagglutination was performed by using PNA (Vector Laboratories Inc., Burlingame, CA 94010) and T-antigen activated human erythrocytes. Stock PNA solution was made by dissolving lyophylized PNA in PBS to a concentration of 40 micro g/ml. Serial twofold dilutions up to 78 ng/ml were made for the assay. Activation of T-antigen on human erythrocytes was performed by washing outdated human Group O blood three times with equal volumes of PBS, centrifugating at 3,000 RPM for 5 minutes and removing of the supernatant. An equal volume of 10% euraminidase (Vibrio cholera neuraminidase, Behring Diagnostics, La Jolla, CA 92037 USA) was added to the packed, washed erythrocytes and incubated at 37° C. for 30 minutes. The erythrocytes were washed again three times and were either used for experiments or stored at 4° C. in an equal volume of Alsiever's solution for future experiments.

Control inhibition of agglutination was performed by using 0.6M D(+)Galactose (Sigma Chemical Company, St. Louis, MO 63178). Ninety-six well polyvinyl microtiter plates (Dynatech, VA) were used, in which each horizontal row of wells was filled with 50 micro l of serial dilutions of PNA solutions, beginning from left 78 ng/ml) to right (40 micro g /ml). The wells in the test row were given 50 micro l of mucus solution followed by incubation at room temperature for 60 minutes to allow for interaction between PNA and the mucus. 50 micro l of the T-antigen activated erythrocytes were then added to each well and incubated at room temperature for 1 hour.

A typical microtiter plate showing the results of this hemagglutination inhibition assay is shown in FIG. 1. The top row shows control hemagglutination inhibition with serial double concentration of PNA from left (78 ng/ml) to right (40 micro g ml). Well No. 1 contains no galactose and therefore acts as a positive control for agglutination. Hemagglutination is inhibited in wells No. 3 (2.5 micro g PNA/ml) through 8 (40 micro g /ml) as indicated by doughnut shaped appearance. Wells 9 through 12 show agglutination of erythrocytes. The bottom row shows a test mucus sample that has inhibited hemagglutination in all wells (No. 3 through 12). Well No. 1 is a control hemagglutination inhibition as performed by the addition of 0.6M D(+)galactose.

The results are shown below in Table 1, from which it can be seen that no false negatives and far fewer false positives (26% vs. about 95%) were found than in the conventional fecal occult blood test:

TABLE 1

Summary of Hemagglutination Inhibition Assay Results*

| Method | Diagnosis | # of Cases Agglutination Inhibition | Total Cases | % Positive |
|---|---|---|---|---|
| Direct Smear of resected colon | Cancer | 5 | 5 | 100 |
| | Normal | 0 | 3 | 0 |
| Rectal Smear from patients | Cancer & Polyps | 6 | 6 | 100 |
| | Non-cancer | 5 | 19 | 26 |

*Age range 35-89 years. "Non-cancer" category includes patients with diverticulosis who are not currently diagnosed to have obvious polyps or cancer. The Fisher exacta test for rectal smear cases was significant at p = 0.0052 (two tailed test).

EXAMPLE 2

Latex Agglutination Test 500 micro l of suspended latex beads (15.8 u diameter, Sigma Chemical Co., St. Louis, Mo.) was centrifuged at 3,000 RPM for 15 seconds and the supernatant was decanted. 500 micro g of peanut agglutinin (Vector Laboratories Ltd., Burlingame, Calif.) was dissolved in 500 micro l of carbonate buffer (pH 9.6) and added to the pellet of latex beads. The pellet was resuspended and incubated at 25° C. for 2 hours with occasional mild shaking to resuspend the beads and allow a more uniform binding. After incubation, the sample was centrifuged at 3,000 RPM for 15 seconds, the supernatant decanted, and the pellet resuspended in PBS (pH 7.4). Any unbound PNA was washed off by repeating the previous step three times. The final pellet was suspended and diluted 1:10 in PBS.

For testing the mucus sample collected during digital rectal examination, 10 micro l of mucus in PBS was added to an equal amount of the latex beads and placed on a glass slide. After five minutes of incubation at 25° C., the slide was read. An agglutination of beads indicating presence of the disaccharide $\beta$-D-Gal-(1->>3)-D-GalNAc was read as positive for cancer, whereas no agglutination after 5 minutes indicated absence of the disaccharide and hence cancer free status.

EXAMPLE 3

Galactose Oxidase Strip Test

This technique uses the ability of galactose oxidase to oxidize the C-6 hydroxyl group of both galactose and N-acetyl galactosamine residues in a complex carbohydrate to D-Galactohexodialdose, then testing for the presence of this oxidized product by basic fuchsin reagent.

Mucus samples were obtained by digital examination with the gloved index finger lubricated with normal saline. The mucus on the examining finger was smeared on the scored side of a piece of membrane filter and sandwiched in waxed paper supplied with Metricel membrane filter 0.45 micro m, (Gelman Sciences, Inc., Ann Arbor, Mich. 48106). The specimens were left to dry for 2 hours at room temperature then saturated with 100 U/ml galactose oxidase Type V, (Sigma Chemicals Co., St. Louis, Mo. 63178) in 0.1M potassium phosphate buffer pH 7.0 and kept in a moist atmosphere at room temperature for 2 hours. The membrane filters were washed in deionized distilled water for 1 min., and placed in Schiff's reagent for 15 min., then placed in running tap water for 10 min. Galactose oxidase 100

U/ml was lyophyllized on a cellulose filter prior to the test which was saturated with deionized distilled water just before the test and placed under the membrane filter (unscored side) and wrapped tightly in a small Parafilm sheet. A color index reference chart was established, on which 1 was considered negative 2, 3 and 4 were considered faint staining and 5 was considered positive, as 5 displayed the most intense pink coloration.

The results are shown below in Table 2, from which it can be seen that no false negatives and far fewer false positives (25% vs. about 95%) were found than in the conventional fecal occult blood test:

TABLE 2

Summary of Galactose Oxidase Assay Results

| Method | Diagnosis | # of Cases With Galactose Oxidase Activity | Total Cases | % Positive |
|---|---|---|---|---|
| Rectal Smear from patients | Cancer & Polyps Non-cancer | 10 4 | 10 16 | 100% 25% |

EXAMPLE 4

Biotinylated Peanut Agglutinin Avidin-Enzyme Assay

PNA was dissolved in carbonate buffer (pH 9) to a final concentration of 100 ng/ml was used to coat the microtiter wells. 10 ng PNA in 100 micro 1 buffer were placed in each well and incubated at 37° C. for 2 hours. The wells were then washed off with phosphate buffered saline (PBS) pH 7.4, after which 100 micro 1 of test mucus (dissolved in PBS) was added to microtiter wells and the mixture incubated at 37° C. for 1 hour. The wells were then washed three times with PBS to remove 100 micro 1 of unbound mucus. Biotinylated PNA (1 micro g /ml) was incubated for an additional hour at 37° C. in order to bind with residual $\beta$-D-Gal-(1->>3)-D-GalNAc (if any). The wells were washed three times with PBS to wash off unbound biotinylated PNA. Avidin-D-alkaline phosphates (Vector Corporation, Burlingame, Calif.) was then added (100 ul/well, 1:50 dilution) to the wells and incubated for 1 hour at 37° C. Following 2 washes with PBS and 3 washes with bicarbonate buffer (pH 9.8), the substrate alpha-p-nitrophenyl phosphate (1 mg/ml) was added to the wells (100 ul/well). Optical absorbance at 405 nm was read after 30 minutes incubation at 37° C. Mucus from known cancer patients were positive while non-cancer patients were negative.

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

Industrial Applicability

As can be seen from the present specification and examples, the present invention is industrially useful in providing easy, simple and inexpensive technique for detection of specific changes accompanying large intestinal cancer with essentially no false negative and very low false positive reactions in addition to detecting premalignant conditions and lesions. The simplicity and low cost of the tests as well as the ability to store its components, including the specimens, open the door for its use as a practical screening test for large intestinal cancer and other diseases of colon and rectum.

What is claimed is:

1. A method for detecting the presence of precancer or cancer of the large intestine, which comprises:
   (a) obtaining a sample of large intestinal mucus from the rectum of a patient;
   (b) assaying said sample to detect the disaccharide marker beta-D-Gal(1->3)-D-GalNAc therein; and
   (c) diagnosing precancer or cancer of the large intestine based upon the presence of the disaccharide detected in the mucus.

2. A process according to claim 1 wherein the disaccharide is detected immunochemically.

3. A process according to claim 1 wherein the discharide is detected quantitatively.

4. A process according to claim 3 wherein the disaccharide is detected by reaction with peanut agglutinin which is immobilized onto a water-insoluble support to form a complex of said disaccharide and the peanut agglutinin.

5. A process according to claim 4 wherein the complex is assayed by reaction with biotinylated peanut agglutinin.

6. A process according to claim 4 wherein the complex is detected by reacting it with avidin which is conjugated with a marker.

7. A process according to claim 1 wherein the assay is performed by use of peanut agglutin in an agglutination inhibition test.

8. A process according to claim 7 wherein the disaccharide is detected by reacting the mucus with an approximately stoichiometric amount of peanut agglutinin.

9. A process according to claim 1 wherein the disaccharide is detected by agglomeration of sensitized beads.

10. A process according to claim 1 wherein the sugar moiety of the disaccharide marker is oxidized and the oxidized sugar moiety is determined.

11. A process according to claim 10, wherein galactose oxidase is used to oxidize the sugar moiety in the mucus.

12. A process according to claim 1 wherein the mucus is absorbed onto a water-insoluble substrate.

13. A process according to claim 12, wherein the water-insoluble substrate is a protein-capturing membrane filter.

14. A process according to claim 1, wherein the mucus is preserved at room temperature for at least several days prior to assaying the sample.

15. A diagnostic kit for detecting the presence of precancer or cancer of the large intestine according to the process of claim 1, which comprises a container comprising separately package galactose oxidase, a water-insoluble support capable of absorbing said large intestinal mucus, and basic fuchsin.

16. A diagnostic kit according to claim 15, wherein the basic fuchsin is package as Schiff's reagent.

* * * * *

UNITED STATES PATENT AND TRADEMARK OFFICE
CERTIFICATE OF CORRECTION

PATENT NO. : 4,857,457
DATED : August 15, 1989
INVENTOR(S) : Shamsuddin et al.

It is certified that error appears in the above-identified patent and that said Letters Patent is hereby corrected as shown below:

TITLE PAGE,

" 16 Claims, 2 Drawing Sheets"

Should read - - - - - -

" 16 Claims, 3 Drawing Sheets "

Signed and Sealed this

Tenth Day of November, 1992

Attest:

DOUGLAS B. COMER

*Attesting Officer*     *Acting Commissioner of Patents and Trademarks*